(12) United States Patent
Wittland et al.

(10) Patent No.: US 7,387,617 B2
(45) Date of Patent: Jun. 17, 2008

(54) NEEDLE SHIELD FOR A GLASS SYRINGE

(75) Inventors: Frank Wittland, Enger (DE); Erhard Stohlmann, Bünde (DE)

(73) Assignee: Gerresheimer Buende GmbH, Buende (DE)

( * ) Notice: Subject to any disclaimer, the term of this patent is extended or adjusted under 35 U.S.C. 154(b) by 90 days.

(21) Appl. No.: 10/912,706

(22) Filed: Aug. 2, 2004

(65) Prior Publication Data

US 2005/0038391 A1    Feb. 17, 2005

(30) Foreign Application Priority Data

Aug. 1, 2003   (EP) .................... 03017423

(51) Int. Cl.
*A61M 5/32* (2006.01)
(52) U.S. Cl. .................... 604/199
(58) Field of Classification Search ............ 604/192, 604/199, 263, 164.08
See application file for complete search history.

(56) References Cited

U.S. PATENT DOCUMENTS

| | | | |
|---|---|---|---|
| 3,865,236 A | 2/1975 | Rycroft | |
| 4,226,333 A * | 10/1980 | Percarpio | 215/247 |
| 4,303,070 A * | 12/1981 | Ichikawa et al. | 604/222 |
| 4,872,552 A | 10/1989 | Unger | |
| 5,344,404 A | 9/1994 | Benson | |
| 6,551,286 B1 | 4/2003 | Claessens | |
| 2002/0062108 A1* | 5/2002 | Courteix | 604/198 |
| 2003/0171719 A1* | 9/2003 | Veillon et al. | 604/187 |
| 2005/0027259 A1* | 2/2005 | Vetter et al. | 604/192 |

FOREIGN PATENT DOCUMENTS

| | | |
|---|---|---|
| EP | 0 592 814 A2 | 4/1994 |
| EP | 0 876 824 A2 | 11/1998 |
| FR | 2 777 787 | 10/1999 |
| WO | 02/074367 A2 | 9/2002 |

* cited by examiner

*Primary Examiner*—Kevin C. Sirmons
*Assistant Examiner*—Catherine N. Witczak
(74) *Attorney, Agent, or Firm*—Laurence A. Greenberg; Werner H. Stemer; Ralph E. Locher

(57) ABSTRACT

The closure stopper and the elastic retaining element are made of gas-permeable material, so that sterilizing gases can penetrate by permeation. The closure stopper is formed of a pharmaceutical rubber. In one variant, the closure stopper, the retaining element and the protective element are made in one piece, with longitudinally extending gas delivery slits arranged between the protective element and the closure stopper.

11 Claims, 4 Drawing Sheets

NEEDLE SHIELD FOR A GLASS SYRINGE

This application claims priority to European Application No. 03 017 423.9 EP filed Aug. 1, 2003.

BACKGROUND OF THE INVENTION

Field of the Invention

The invention relates to a needle guard for a glass syringe, having a closure stopper, a retaining element with substantially the shape of a hollow cylinder and with an opening for receiving a portion of a syringe body of the glass syringe, and an associated protective element with substantially the shape of a hollow cylinder, the closure stopper and the retaining element being made of an elastic material and the protective element being made of a harder material.

It is known that glass syringes with needles which are generally connected permanently to the syringe body, for example by adhesive means, can be closed with a push-on needle guard made of elastic material, such as rubber. This needle guard surrounds the needle and can be easily pulled off. Such a needle guard is described in U.S. Pat. No. 3,865,236, inter alia.

Problems arise if the glass syringe is exposed to different temperatures or air pressures. Glass syringes are generally sterilized after they have been filled with a liquid, for example containing pharmaceutical active substances, and have been closed with the known needle guard.

In doing this, they are exposed to high temperatures, for example 121° C. or 134° C., and to a vacuum, so that the elastic needle guard expands. This often leads to loosening of the needle guard and to its slipping from the glass syringe. Thus, during sterilization, the needle guard often detaches from the glass syringe (pop-off effect).

SUMMARY OF THE INVENTION

The object of the present invention is to make available a needle guard in which the above-described loosening is avoided and the delivery of sterilizing gases by permeation is improved. In addition, a needle guard is to be made available in which subsequent manipulation of the content of the syringe can be immediately detected.

In the case of a needle guard of the generic type concerned, this object is achieved by the fact that the closure stopper and the elastic retaining element are made of gas-permeable material, with the gas being intended for sterilization. In one embodiment of the invention, openings are arranged in the protective element at the level of the closure stopper, said closure stopper advantageously being made of a pharmaceutical rubber. The pharmaceutical rubber can be made of SBR or NBR or BIIR or CIIR. According to one feature of the invention, apertures extending transversely with respect to the longitudinal axis are arranged in the protective element at the level of the upper limit of the syringe body, at the start of the syringe cone.

In one variant of the invention, in the case of a one-piece configuration of the closure stopper, retaining element and protective element, longitudinally extending gas delivery slits are arranged between the protective element and the closure stopper. It is possible, underneath the gas delivery slits, to guide the retaining element through the protective element as far as the outer limit of the protective element, by which means an additional form-fit connection is established and passage of gas is permitted. The retaining element can have steps on its outside wall. The retaining element advantageously has a catch element which can be locked together with a catch element of the syringe body, the catch element of the retaining element being formed by an inwardly directed annular bead, and the catch element of the syringe body being formed by an annular groove.

Advantageous embodiments of the invention are set out in the other dependent claims.

Illustrative embodiments of the invention are explained below.

DESCRIPTION OF THE PREFERRED EMBODIMENTS

Figure 1:
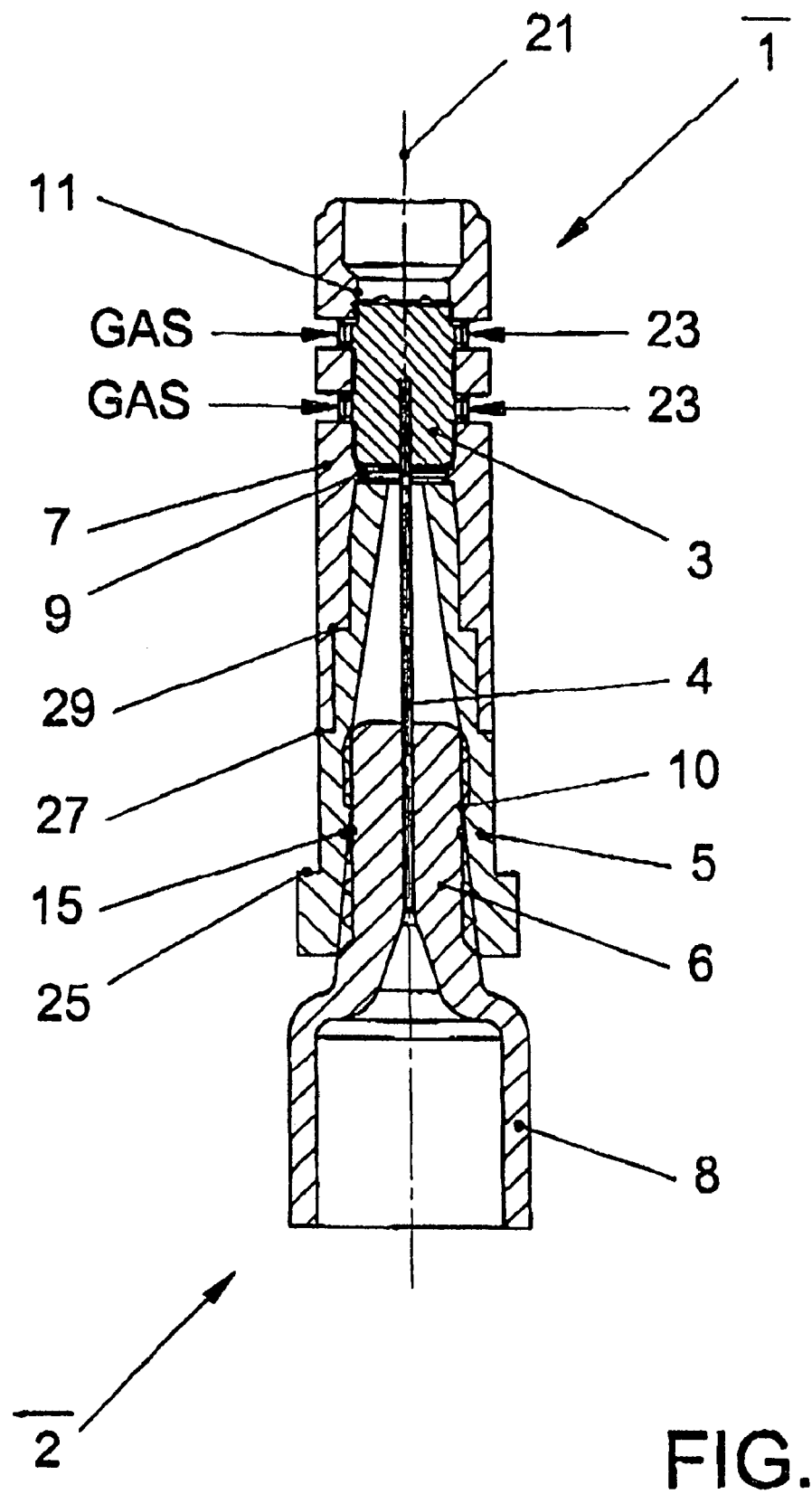
FIG. 1 shows a vertical section through a needle guard with closure stopper, pushed onto a glass syringe.

According to FIG. 1, the needle guard 1 has a retaining element 5, a protective element 7 and a closure stopper 3. The retaining element 5 consists of an elastic material, for example a thermoplastic, vulcanized elastomer (TPE-V). It is designed substantially in the shape of a hollow cylinder which has steps 25, 27, 29 on its outer walls. In the state when pushed on, the cylindrical retaining element 5 receives a portion 6 of the syringe body 8 of the glass syringe 2. The retaining element 5 has different external diameters, the external diameter of the end portion directed toward the glass syringe 2 being the greatest, and the external diameter of the other, opposite end portion being the smallest. The external diameter of the last-mentioned end portion of the retaining element 5 is chosen such that it can be received by the protective element 7.

In the state when pushed on, the retaining element 5, by virtue of its elasticity, holds the needle guard 1 on the glass syringe 2 and seals off the inside of the needle guard 1.

The protective element 7 is made of a dimensionally stable material, for example polypropylene, which is minimally elastic compared to the retaining element 5 and the closure stopper 3. The protective element 7 is designed substantially as a hollow cylinder which, after the needle guard 1 has been fitted on the glass syringe 2, surrounds the needle 4. The cylindrical protective element 7 can have different internal diameters along its longitudinal axis 21, the internal diameter of the end portion directed toward the retaining element 5 being of such dimension that the corresponding end portion of the retaining element 5 can be received. The other end portion of the protective element 7 has an internal diameter which is such that the closure stopper 3 can be received. The protective element 7 and the retaining element 5 are produced as one piece by means of a two-component injection-molding operation and permanently connected to one another, the protective element 7 being made of PP, and the retaining element being made of TPE-V. The protective element 7 is open at its end directed away from the syringe, although it could also be closed. It has two holders 9, 11 which hold the closure stopper 3 at a predetermined position. In the area of the closure stopper 3, the protective element 7 has openings 23 which, in this illustrative embodiment, are of elongate design and extend transversely with respect to the longitudinal axis 21 of the substantially cylindrical protective element 7. The purpose of the openings 23 is to allow sterilizing gases to pass by permeation through the closure stopper 3.

The closure stopper 3 is made of an elastic pharmaceutical rubber, for example SBR (styrene-butadiene rubber) or NBR (nitrile-butadiene rubber) or BIIR (bromo isobutene-isoprene rubber) or CIIR (chloro isobutene-isoprene rubber) and is gas-permeable. The closure stopper 3 is of cylindrical design and has an external diameter which is substantially equal to the internal diameter of the end portion of the protective element 7 directed away from the syringe body 8. In the state when fitted, the needle 4 of the glass syringe 2 penetrates into the closure stopper 3, so that the needle 4 is sealed.

Since the needle guard 1 according to the invention consists to a large extent of the protective element 7, which has scarcely any elasticity compared to the retaining element 5 and the closure stopper 3, undesired loosening of the needle guard 1 caused by different temperatures or air pressures rarely takes place.

Figure 2:
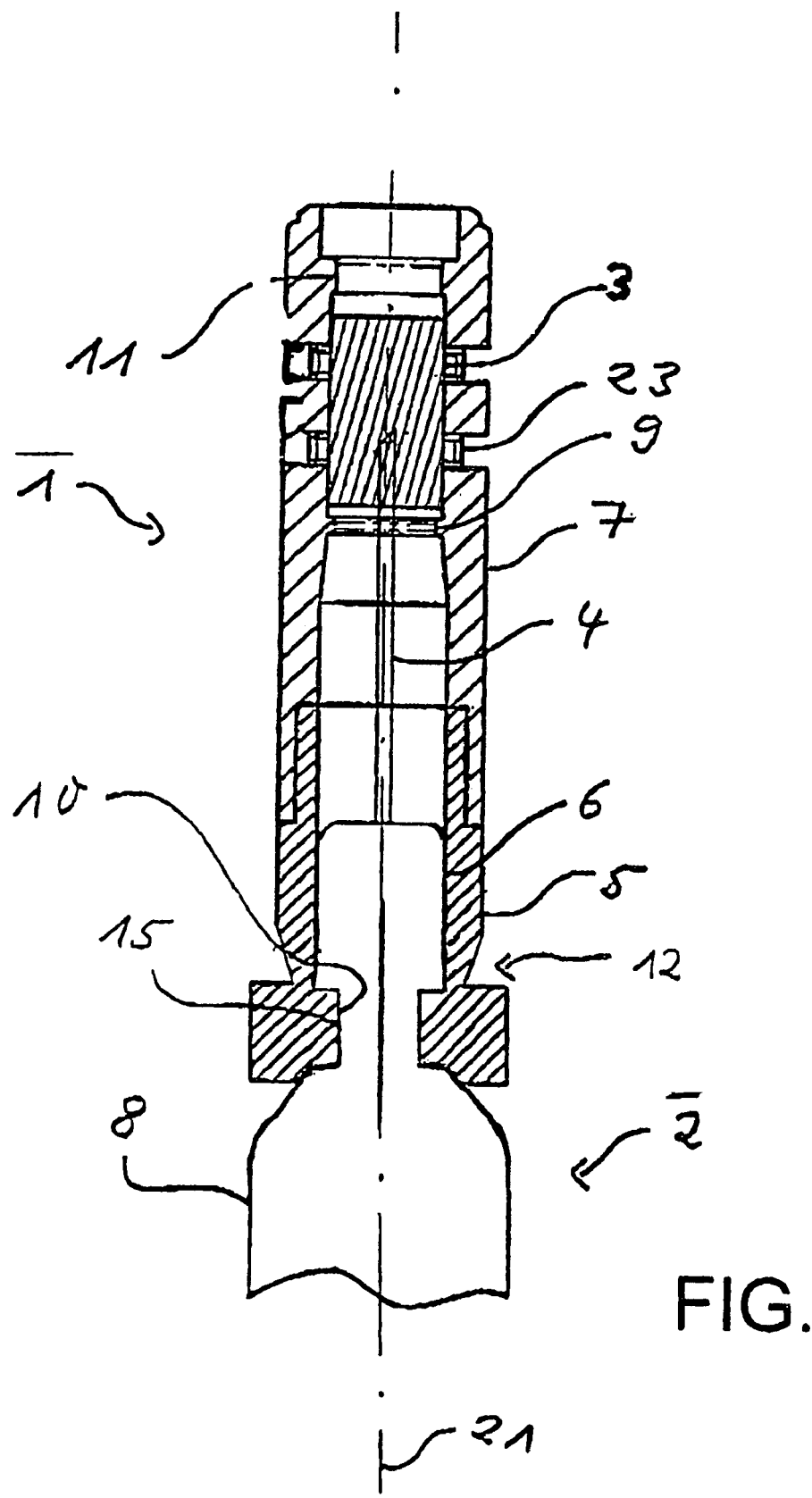
FIG. 2 shows a vertical section through a further embodiment of a needle guard, pushed onto a glass syringe.

A further embodiment is shown in FIG. 2. Here too, the needle guard 1 according to the invention consists of a retaining element 5, a protective element 7 and a closure stopper 3.

Whereas the protective element 7 and the closure stopper 3 are unchanged compared to the first embodiment, the retaining element 5 in this case has a catch element 15 which, in the state shown in FIG. 2, is locked securely to a catch element 10 of the syringe body 8. The catch element 15 of the retaining element 5 is an annular bead, and the catch element 10 of the syringe body 8 is an annular widening or recess. In this way, the retaining element 5 is connected permanently to the syringe body 8. In other illustrative embodiments, the retaining element 5 could also be connected securely to the syringe body 8 by other connecting means, for example by adhesive means. The retaining element 5 has, adjacent to the side of the catch element 15 directed away from the syringe body 8, a predetermined breaking point 12 designed as a circumferential cross-sectional weakening. The predetermined breaking point 12 can also be formed in some other way, for example by slits. The purpose of the predetermined breaking point is to make manipulation of the content of the syringe immediately apparent. When the needle guard 1 according to the illustrative embodiment shown in FIG. 2 is removed, the catch element 15 is separated from the retaining element 5 at the predetermined breaking point 12 and remains on the syringe body 8. If the needle guard 1 damaged in this way is pushed back onto the glass syringe 2, the previous removal of the needle guard 1 is detectable from the retaining element 5 broken through at the predetermined breaking point 12.

Figure 3:
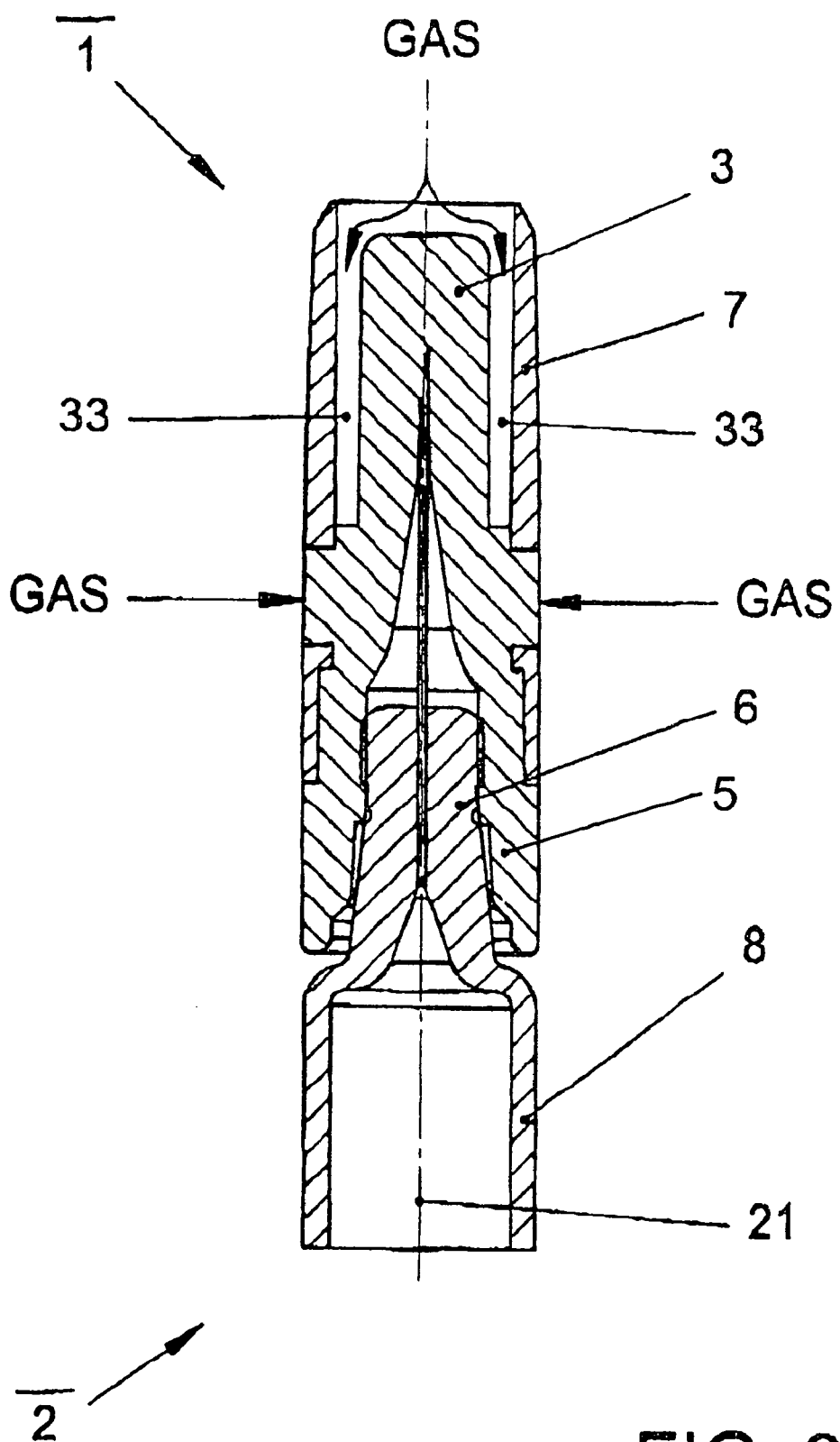
FIG. 3 shows a vertical section through a further embodiment of a needle guard, pushed onto a glass syringe.

FIG. 3 shows a further embodiment. Compared to the embodiments according to FIG. 1 and FIG. 2, the closure stopper 3, the retaining element 5 and the protective element 7 are produced as one piece in a two-component injection-molding operation, the closure stopper 3 and the retaining element 5 being made of an identical elastic material, and the protective element 7 being made of a harder material. The gas delivery according to FIG. 3 takes place via longitudinally extending gas delivery slits 33 which run between the protective element 7 and the closure stopper 3.

Figure 4:
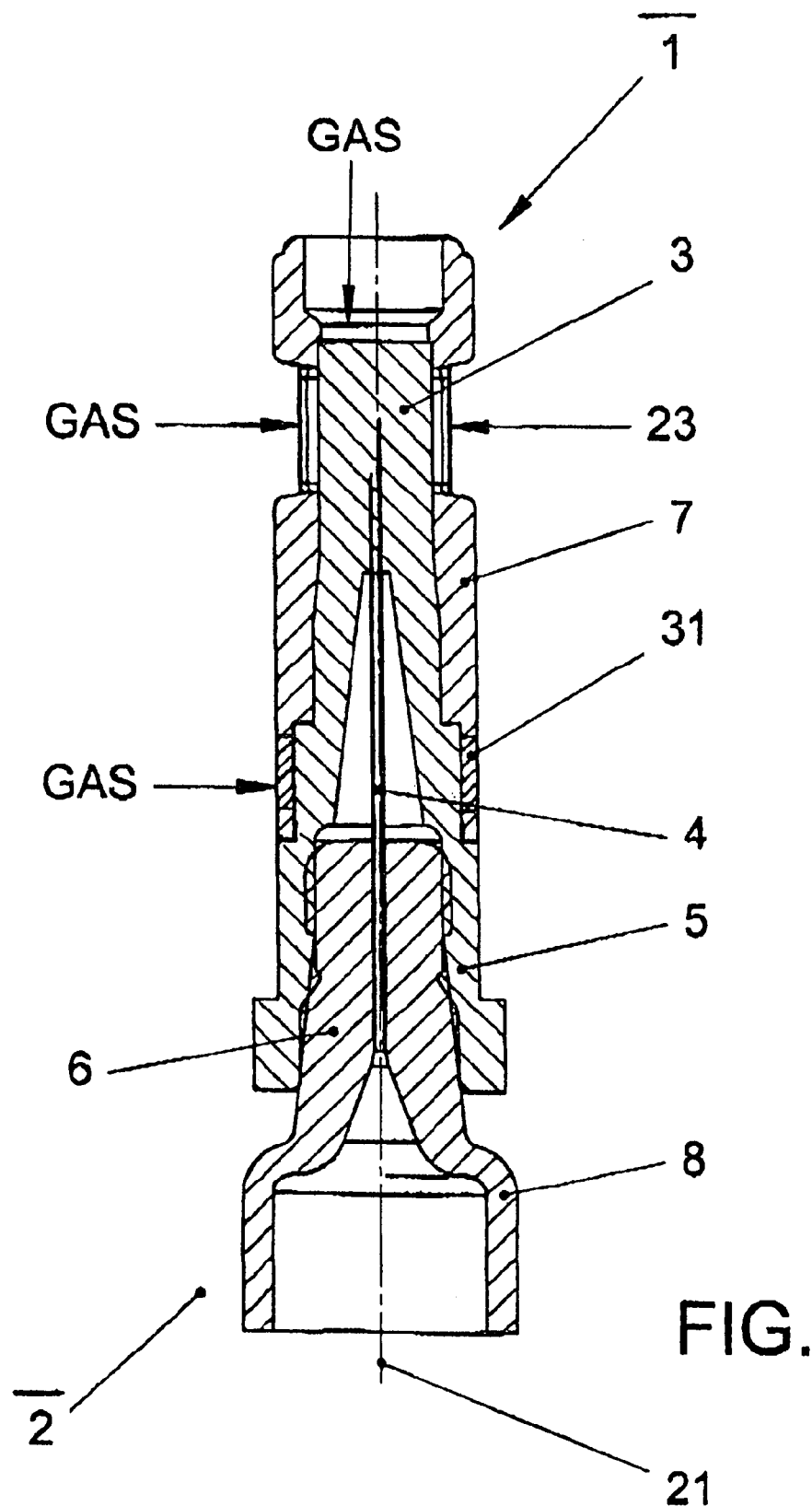
FIG. 4 shows a vertical section through a further embodiment of a needle guard, pushed onto a glass syringe.

In contrast to the embodiment according to FIG. 3, the gas delivery according to FIG. 4 does not take place through longitudinally extending slits 33, but instead via openings 23 arranged in the upper area of the protective element 7 and extending transversely with respect to the longitudinal axis, and additionally via apertures 31 extending transversely with respect to the longitudinal axis 21 in the protective element 7 at the level of the lower area of the needle 4.

The protective element 7 can have ribs on its outside wall, which ribs, for example, can be arranged parallel to the longitudinal axis 21 of the protective element 7. The ribs improve the grip of the protective element 7.

We claim:

1. A needle guard for a glass syringe with a needle having a longitudinal axis, the needle guard comprising:
    a closure stopper;
    a retaining element having a substantially hollow cylinder shape and an opening formed therein for receiving a portion of a syringe body of the glass syringe;
    a protective element having a substantially hollow cylinder shape and receiving a portion of said retaining element and said closure stopper, said protective element having a section with a continuous circumferential wall surrounding said closure stopper said closure stopper and said retaining element made of an elastic material and said protective element made of a harder material being harder than said elastic material, said closure stopper and said retaining element made of a gas-permeable material permeable to a gas used for sterilization; and
    longitudinal slits extending along the longitudinal axis formed between said closure stopper and said section of said protective element, said longitudinal slits extending towards said opening of said retaining element, said longitudinal slits configured for extending along a length of the needle when the needle guard is attached to the syringe.

2. The needle guard according to claim 1, wherein said retaining element is formed of thermoplastic elastomer TPE-V, and said protective element is formed of thermoplastic PP for forming a permanent connection.

3. The needle guard according to claim 1, wherein said closure stopper is made of a pharmaceutical rubber.

4. The needle guard according to claim 1, wherein said closure stopper is made of a material selected from the group consisting of SBR, NBR, BIIR and CIIR.

5. The needle guard according to claim 1, wherein said closure stopper, said retaining element and said protective element form a one-piece unit, said one-piece unit having longitudinally extending gas delivery slits formed between said protective element and said closure stopper.

6. The needle guard according to claim 5, wherein underneath said gas delivery slits, said retaining element is guided partially through said protective element as far as an outer limit of said protective element.

7. The needle guard according to claim 1, wherein said retaining element has a first catch element that can be locked together with a second catch element of the syringe body.

8. The needle guard according to claim 7, wherein said first catch element of said retaining element is formed as an inwardly directed annular bead, and the second catch element of the syringe body is formed by an annular widening or recess.

9. The needle guard according to claim 7, wherein said first catch element of said retaining element can be separated from said retaining element upon removal of the needle guard from the glass syringe.

10. A needle guard for a glass syringe having a syringe body and a needle having a longitudinal axis, the needle guard comprising:
    a closure stopper configured for being penetrated by the needle thereby sealing the needle, said closure stopper configured for engaging a portion of the syringe body, said closure stopper being formed of an elastic material, said elastic material being gas-permeable material permeable to a gas used for sterilization;

a protective element having a substantially hollow cylindrical shape, said protective element having a section with a continuous circumferential wall surrounding said closure stopper, and said protective element receiving a portion of said closure stopper; and longitudinal slits extending along the longitudinal axis formed between said closure stopper and said section of said protective element, said longitudinal slits extending towards said opening of said retaining element, said longitudinal slits configured for extending along a length of the needle when the needle guard is attached to the syringe.

11. The needle guard according to claim 10, wherein said protective element is formed of material that is harder than said elastic material.

* * * * *